Figure 1:
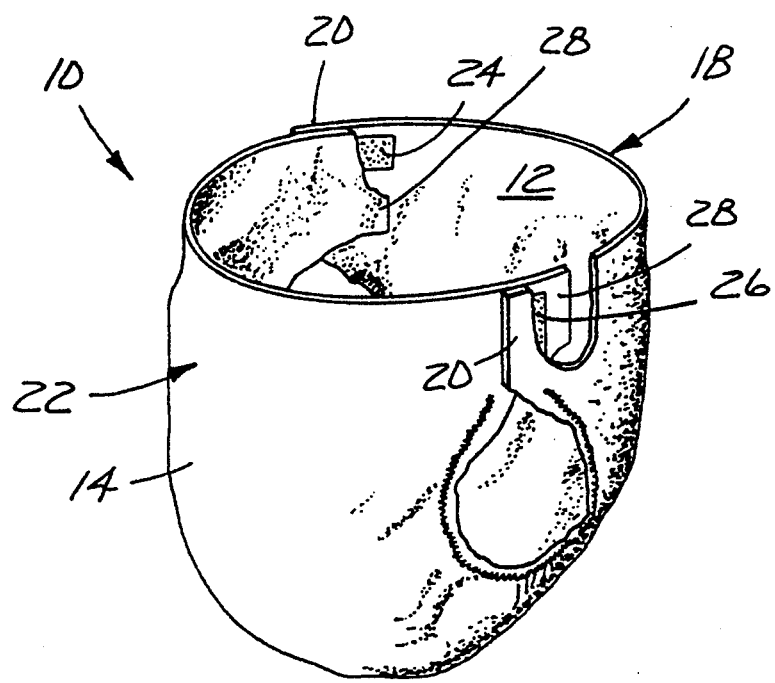

United States Patent [19]

Miller et al.

[11] Patent Number: 5,389,438
[45] Date of Patent: Feb. 14, 1995

[54] REPOSITIONABLE ADHESIVE TAPE

[75] Inventors: John A. Miller; George J. Clements, both of St. Paul, Minn.

[73] Assignee: Minnesota Mining and Manufacturing Company, St. Paul, Minn.

[21] Appl. No.: 681,655

[22] Filed: Apr. 8, 1991

Related U.S. Application Data

[63] Continuation of Ser. No. 483,130, Feb. 22, 1990, abandoned.

[51] Int. Cl.$^6$ ............................................. C09J 7/02
[52] U.S. Cl. ................................. 428/355; 428/512; 525/98; 525/99
[58] Field of Search .................. 428/355, 512; 525/95, 525/98, 99

[56] References Cited

U.S. PATENT DOCUMENTS

| | | | |
|---|---|---|---|
| 2,649,856 | 8/1953 | Le Bolt | 128/284 |
| 2,714,562 | 8/1955 | Hechtman | 117/68.5 |
| 2,962,404 | 11/1960 | McIntyre et al. | 154/46 |
| 3,049,228 | 8/1962 | Burnett | 206/58 |
| 3,239,478 | 3/1966 | Harlan, Jr. | 260/27 |
| 3,635,861 | 1/1972 | Russell | 260/27 |
| 3,638,651 | 2/1972 | Torr | 128/284 |
| 3,917,607 | 11/1975 | Crossland et al. | 260/28.5 B |
| 3,932,328 | 1/1976 | Korpman | 260/27 BB |
| 3,954,692 | 5/1976 | Downey | 260/33.6 AQ |
| 4,104,327 | 8/1978 | Inoue et al. | 525/99 X |
| 4,136,699 | 1/1979 | Collins et al. | 525/99 X |
| 4,189,547 | 2/1980 | Osborn et al. | 525/99 |
| 4,288,567 | 9/1981 | Feeney et al. | 525/99 |
| 4,399,249 | 8/1983 | Bildusas | 524/271 |
| 4,418,123 | 11/1983 | Bunnelle et al. | 428/152 X |
| 4,514,554 | 4/1985 | Hughes et al. | 526/339 |
| 4,522,874 | 6/1985 | Pommez | 428/284 |
| 4,652,491 | 3/1987 | Gobran | 525/99 X |
| 4,684,685 | 8/1987 | Schuman et al. | 524/270 |
| 4,717,749 | 1/1988 | Tang et al. | 524/271 |
| 4,728,572 | 3/1988 | Davis . | |
| 4,761,341 | 8/1988 | Rosiak et al. | 428/512 |
| 4,778,701 | 10/1988 | Pape et al. | 428/40 |
| 4,780,367 | 10/1988 | Lau et al. | 428/355 |
| 4,785,043 | 11/1988 | Kawai et al. | 525/99 X |
| 4,813,947 | 3/1989 | Korpman | 604/387 |
| 4,833,193 | 5/1989 | Sieverding | 524/486 |
| 4,861,635 | 8/1989 | Carpenter et al. | 428/40 |
| 4,906,691 | 3/1990 | Joseph et al. | 525/99 |
| 5,019,071 | 5/1991 | Bany et al. | 604/389 |
| 5,019,072 | 5/1991 | Polski | 604/389 |
| 5,028,646 | 7/1991 | Miller et al. | 524/77 |

FOREIGN PATENT DOCUMENTS

| | | | |
|---|---|---|---|
| 74595/87 | 1/1988 | Australia | A61F 13/16 |
| 11700/88 | 9/1988 | Australia | B42C 11/00 |
| 20442/88 | 4/1989 | Australia | C09J 3/14 |
| 0260873 | 3/1988 | European Pat. Off. | C09J 3/14 |
| 1918626 | 10/1969 | Germany . | |
| 63-189485 | 6/1988 | Japan | C09J 3/14 |
| 138280 | 4/1989 | Japan . | |
| 118604 | 10/1989 | Japan . | |
| 2116253B | 9/1965 | United Kingdom | A44B 18/00 |
| PCT/EP88/-00176 | 9/1989 | WIPO | C08L 53/02 |

*Primary Examiner*—Jenna L. Davis
*Attorney, Agent, or Firm*—Gary L. Griswold; Walter N. Kirn; William J. Bond

[57] ABSTRACT

An adhesive of certain elastomeric block copolymers and tackifying materials can be hot-melt coated onto a flexible backing to provide an adhesive tape, two pieces of which can bond to each other to have excellent resistance to shear forces but can be easily peeled apart, even after prolonged periods of time. The adhesive can be low-tack or tack-free. When the novel adhesive is tacky, it can bind sheets into a note pad from which individual sheets can be removed, temporarily adhered to paper and other substrates, and later cleanly removed, even after prolonged contact.

8 Claims, 1 Drawing Sheet

REPOSITIONABLE ADHESIVE TAPE

This is a continuation of application Ser. No. 07/483,130, filed Feb. 22, 1990, now abandoned.

BACKGROUND OF THE INVENTION

1. Field of the Invention

The invention is concerned with low-tack and tack-free adhesives that substantially do not experience adhesion build-up and so provide tapes that are repositionable, even after being adhered to a substrate for prolonged periods of time. Of special interest are low-tack pressure-sensitive adhesive note pads and adhesive diaper closures.

2. Description of the Related Art

POST-IT ™ note pads have become virtually indispensable in the office, each sheet bearing a stripe of pressure-sensitive adhesive that is sufficiently tacky to adhere to paper and other substrates but does not show a buildup of adhesion. The sheets can be cleanly removed and reapplied a number of times without loss of tackiness. These attributes are realized due to the use of tacky microspheres coated onto the paper substrate, as disclosed in U.S. Pat. No. 3,691,140 (Silver). The same low-tack pressure-sensitive adhesive has been used for a number of other purposes, e.g. as a coating for a bulletin board or for posting ordinary pieces of paper.

The widespread success of the POST-IT ™ note pads and the relatively high cost of the adhesive have resulted in efforts to produce a pressure-sensitive adhesive of a more simple, and hence more economical, composition that would provide the same attributes. However, it is believed that every known pressure-sensitive adhesive has been deficient in some important respect, e.g., being too aggressively tacky or lacking the desired initial holding power or being subject to a gradual buildup in adhesion.

An adhesive that is said to afford similar properties as that used in POST-IT ™ note pads is the subject of U.S. Pat. No. 4,684,685 (Shuman et al.). Shuman et al.'s preferred adhesive includes a natural rubber latex and a tackifier which is an anionic aqueous dispersion of hydrogenated rosin or rosin esters. After coating the dispersion onto a substrate such as a sheet of paper, the dried coating allegedly has enough tack to adhere to solid contact surfaces by manually pressing the coated substrate to that surface. The Shuman patent says that the user can then "reapply the coated substrate as many as eight to ten additional times to the same or another free solid surface."

Although there have been attempts at providing alternative adhesive formulations which provide properties suitable for use as a repositionable adhesive, such as for repositionable note pads, there is still great interest in the discovery of yet more alternatives.

Of additional interest for repositional low-tack adhesives, and otherwise, are adhesives which adhere to themselves yet are subsequently removable and re-adherable. Adhesives with these properties may or may not have repositionable tape or note pad properties. Advantageously, for certain applications these self-adhering adhesives will be relatively non-tacky or have no tack so that they exhibit adhesiveness to little else other than itself. Examples of such adhesives are discussed in U.K. Pat. No. GB 2,116,253B (Clerici et al.) and U.S. Pat. No. 4,522,874 (Pommez).

Clerici et al. releasably joins two objects using two pieces of "adhesive" tape that can be repeatedly engaged and disengaged. They state that this requires each of (a) the cohesive strength of the carriers, (b) the anchoring of the adhesive layers to the carriers, and (c) the cohesive strength of the adhesive layers to be stronger than the force required to separate two engaged tapes. The Clerici et al. adhesive can be coated from "an elastomer for example natural rubber dissolved in a solvent such as heptane in the proportions of 15% natural rubber and 55% of heptane, by weight" (sentence bridging pages 8 and 9). Also useful is "a mixture of elastomeric materials, consisting for example of natural rubber and elastomers of a synthetic nature, such as butadiene-styrene rubber" (page 4, lines 17-24). The Clerici et al. "adhesive" is just rubber or a mixture of natural and synthetic rubber which is attached to an, e.g., cloth backing.

Pommez illustrates a three-layer disposable diaper, the outer layer of which is "a porous paper-like substrate having one surface thereof coated with a selective adhesive which adheres only to itself" (col. 2, lines 38-41). Referring to FIG. 2: "Ears, or projections 54, of the back portion of the diaper, are also impregnated with the adhesive of the invention from inside, which enables its selective adhesion in any position on the outer surface, also impregnated, of the front portion 56, of the diaper. The qualities of the invention's adhesive enable the fastening and refastening of ear 54 until a perfect fit on the wearer's body is obtained, or permits the diaper to be removed and used again later" (col. 4, lines 1-11). "The adhesive is comprised of an aqueous ammoniacal emulsion having about 60 percent solids and about 0.003 percent ammonia. The solids are about 85 parts by weight poly-cis-isoprene and about 15 parts by weight vinyl acetate and n-butyl acrylate" (col. 2, lines 41-45).

This emulsion of Pommez serves as an adhesive and as the means by which the outer shell (paper) is made water impermeable. There is no indication that this emulsion would be suitable for use in a tape or on a diaper which is not a porous paper substrate, e.g. a polyolefin backing which would severely limit the applicability of this self-adhering adhesive. Further use of a solvent based system is hampered by the need to subsequently remove and properly dispose of the solvent. This problem is particularly acute where the solvent is a volatile organic, as in Clerici et al.

The present invention has as a general object to solve or substantially alleviate the above noted problems in the art.

Another object of the invention is to provide an adhesive composition that is self-adhering.

A more specific object is to provide a self-adhering adhesive that can be subsequently removed and reapplied to itself.

A more specific object is to provide a self-adhering adhesive which is suitable for use as a repositionable diaper closure.

Another more specific object is to provide a self-adhering adhesive that has low or no adhesive buildup to itself.

Another object is to provide a repositionable adhesive.

A more specific object is to provide a repositionable adhesive which is adhesive to itself.

A further object of the present invention is to provide a method for applying these adhesives without the use of a solvent.

Further advantages and features of the invention, as well as the scope, nature and utilization of the invention will become apparent to those skilled in the art from the following description of the preferred embodiments of the invention.

SUMMARY OF THE INVENTION

The invention provides a low-tack or tack-free adhesive that can be coated onto a backing, generally flexible, to provide an adhesive tape, two pieces of which can bond to each other with excellent resistance to shear forces while still being easily peeled apart, even after prolonged periods of time. When the novel adhesive composition is low-tack, it is a pressure-sensitive adhesive and can have the attributes of the adhesives of the Silver patent, while being more economical to manufacture because it is hot-melt coatable and does not require tiny balls of a stiff pressure-sensitive adhesive or cause the environmental problems of solvent coating methods. Briefly, the novel adhesive comprises a composition of by weight:

from 20 to 80 parts of at least one elastomeric block copolymer selected from styrene/butadiene, styrene/isoprene, and styrene/ethylene-butylene block copolymers, and correspondingly from 80 to 20 parts of tackifying material selected from tackifier resins or blends and blends of tackifier resin with liquid plasticizer oil, which adhesive can be hot-melt coated without the use of solvents and has a composite midblock glass transition temperature (CMTg) from 225 Kelvin to 240 Kelvin when the adhesive is based on styrene/isoprene or styrene/ethylene-butylene block copolymers and a CMTg from 215 Kelvin to 235 Kelvin when the adhesive is based on styrene/butadiene block copolymer. The CMTg can be calculated using the Fox Equation from the measured Tg of the midblock of the elastomeric block copolymer and the measured Tg of each tackifying resin and liquid plasticizer oil. The Tg for each component is measured using a differential scanning calorimeter such as a DSC-7, manufactured by Perkin-Elmer. The Tg is measured on the second heating run using a scan rate of 20 degrees Centigrade per minute. The first heating run is made up to well above the softening point of the test material. The sample is subsequently quenched to well below the Tg of the material. Antioxidants added to the adhesive are not figured into the calculation of the CMTg.

Fox Equation $$\frac{\Sigma_i W_i}{CMTg} = \Sigma_i \frac{W_i}{Tg_i}$$

where $W_i$ is the weight fraction of component i and $Tg_i$ is the glass transition temperature of component i. Only the midblock portion of the block copolymer is included in the calculation of the CMTg. For a styrene/isoprene block copolymer, the midblock portion is the polyisoprene portion of the molecule.

The tackifier resin or blend, or blend of tackifier resin(s) and liquid plasticizer oil(s) of the novel adhesive can be any of solid tackifier resin(s), liquid tackifier resin(s), blend of a solid tackifier resin(s) and liquid tackifier resin(s), a blend of a solid tackifier resin(s) and liquid plasticizer oil(s), and a blend of solid tackifier resin(s), liquid tackifier resin(s), and liquid plasticizer oil(s).

The blends are preferred, because they give a formulator more control over the rheological properties of the adhesive than does the use of a single tackifier resin. For example, when the proportion of elastomeric block copolymer is near the high end (i.e., 55–80 parts) and the CMTg is near the high end (i.e., within 10 Kelvin) of the aforementioned ranges, the novel adhesive tends to have high resistance to shear forces and to be low-tack or tack-free. This type of adhesive will be best suited for use as a self-adhering adhesive. Its low, or no, tack makes it have little or no adhesion to other substrates while its high resistance to shear when attached to itself makes it ideal for a reuseable adhesive closure system.

On the other hand, the novel adhesive can be somewhat tacky when the proportion of elastomeric block copolymer is near the low end (i.e., 20–45 parts) and the CMTg is near the high end of those ranges. These adhesives are generally usable as repositionable adhesive tapes, however, they will have a tendency to buildup adhesion over extended periods of time. These adhesives however will still be self-adhering and show the characteristics discussed above.

The least buildup of adhesion to other substrates is realized when both the proportion of elastomeric block copolymer and the CMTg are relatively low. These adhesives are the best suited for use as a repositionable tape on note pads, such as is used in a Post-it ™ pad. These tapes, however, will still display self adhesion properties, although generally with lower shear resistance.

Overall, the lower buildup of adhesion to other substrates seems to be primarily related to CMTg while the tendency to build up adhesion to itself seems to be primarily a function of percent polymer concentration. However, these observations are merely generally noted trends, and suitable adhesives for, e.g., self-adhering tape applications or repositionable tapes can be found outside the most likely areas to find such tapes within the invention composition.

In addition to the foregoing components, the adhesive of the invention can incorporate small amounts of other materials commonly used in pressure-sensitive adhesives, e.g. antioxidants such as hindered phenols and hydroquinones, heat stabilizers such as zinc carbamates, ultraviolet stabilizers, fillers, and pigments. Such additional materials can be disregarded in the CMTg calculation.

The adhesive of the invention can be economically converted to tapes by being coated onto backings at high speeds without the use of solvents, or can be coated from solution when that is more convenient. Depending on the backing, the backings can be surface treated to promote adhesion of the adhesive thereto. The resulting tapes can be marketed in strips or in wide sheets and usually have flexible backings for ease of storage, handling, and application. For example, stripes of the novel adhesive can be coated onto paper which is then cut and stacked to form a tablet or note pad of repositionable sheets like the aforementioned POST-IT ™ note pads. For such use, the adhesive is preferably somewhat tacky so that sheets of a note pad will adhere temporarily to paper and other substrates from which they can later be cleanly removed.

For uses requiring the adhesive to be somewhat tacky, such as for a repositionable note pad, the CMTg can be as low as 220 Kelvin when the adhesive is based on styrene/isoprene or styrene/ethylene-butylene block copolymers which comprise up to 45% by weight of the adhesive.

Whether or not the novel adhesive is low-tack or tack-free, pieces of tape bearing the adhesive have a remarkable ability to form bonds to each other that have excellent resistance to shear forces. In tests, even after four months at ordinary room temperatures, two tapes bearing the novel adhesive separate cleanly between their adhesive layers. The same tapes also separate cleanly after two hours at 37° C. However, low tack adhesives with properties best suited for use as a repositionable adhesive have a tendency to block slightly at above ambient temperatures (e.g., at 37° C.). Therefore, these adhesives would not be as desirable for self-adhering adhesive closures used in close contact with a heated body, such as in a diaper closure system.

In any event, the ability of certain inventive compositions to separate cleanly after 2 hours at 37° C. would make these inventive adhesives well suited for reclosable apparel closures that are used in close proximity to the wearer. Examples of uses for such closure systems include diapers, incontinence devices, surgical gowns, hats or booties, clean room garments, ankle bands, wrist bands or the like. When used, as in reclosable apparel closures, the adhesive can be directly applied to the article or applied as a tape where the side which is permanently attached to the article can have a suitable conventional adhesive. The adhesive would generally be applied as patches on each side of a closure point, e.g., on opposing faces of at least two closure elements that mate to complete the closure. When the two closure elements of the article are brought into contact the adhesive patches will come into contact yielding a resealable closure. The patches can be of a size and arrangement such that they will contact each other over a number of overlapping positions of the closure elements to form an adjustable closure.

For example, the novel adhesive can be used to provide a reclosable disposable diaper by applying a patch of the adhesive to the inner face of each of the corners at the back of a disposable diaper and also to the outer shell where the front of the diaper can be overlapped by the corners when the diaper is wrapped around the waist of a person. The face-to-face contact between those adhesive patches holds the diaper securely in place, but these patches can be easily peeled apart, either to remove or to refasten the diaper.

Where a closure system is used at ambient conditions generally any adhesive composition of the invention can be used with suitable adjustment of the size, shape, and location of the adhesive patches to account for slight variations in the strength of the adhesive bonding strength.

The novel adhesive also can be used to permit labels and masking tapes to be cleanly removed from substrates to which they may be applied. Other useful tape articles of the invention that have flexible backings include reclosable mailing envelopes, resealable bags, adhesive-backed sandpaper and sanding disks, and decals. The novel adhesive also can be marketed in a spray can from which layers can be applied for uses such as temporarily mounting posters or photographs.

DETAILED DISCLOSURE

Elastomeric block copolymers that are useful in the adhesive of the invention can have any of the common configurations of the block structure including linear diblock and triblock, radial, star, and tapered geometries. Useful elastomers include styrene/isoprene block copolymers such as "Kraton" 1107 and "Kraton" 1111, available from Shell Chemical Co.; "Enichem" SOL T 190, available from Enichem USA; "Quintac" 3421, "Quintac" 3430 and "Quintac" 3530, available from Nippon-Zeon; Finaprene 424, available from Fina Chemical Co.; styrene/butadiene block copolymers such as "Kraton" 1101 and 1102; "Stereon" 840A, available from Firestone Synthetic Latex and Rubber Co., and "Enichem" Sol T 1205 and Sol T 161 C; and styrene/ethylene-butylene block copolymers such as "Kraton" 1657 and 1650.

Tackifier resins that are useful in the novel adhesives include those aliphatic hydrocarbon resins made from the polymerization of a feed stream consisting mainly of unsaturated species containing four to six carbon atoms, such as "Wingtack" 10, "Wingtack Plus", and "Wingtack" 95, available from the Goodyear Tire and Rubber Co., "Escorez" 1310, available from Exxon Chemical Co., and "Hercotac" RT-95, available from Hercules, Inc.; rosin esters and rosin acids such as "Hercoflex" 400, "Hercoflex" 500, "Foral" 85, "Regalite" 355, and "Permalyn" 305, all available from Hercules, Inc.; mixed aliphatic/aromatic liquid tackifiers such as "Escorez" 2520 available from Exxon Chemical Co.; and polyterpene tackifiers such as "Zonarez" A-25 and "Zonarez" A-100, available from Arizona Chemical Co. and "Piccolyte" HM-85, HM-105, and S-115 available from Hercules, Inc. Also useful are the general class of hydrogenated tackifying resins, including ECR-327, "Escorez" 5380, "Escorez" 5300, "Escorez"5320, and "Escorez" 5340, all available from Exxon Chemical Co.; "Regalrez" 1018, "Regalrez" 1065, "Regalrez" 1078, "Regalrez" 1094, and "Regalrez" 1126, all available from Hercules Inc.; and "Arkon" P-90, "Arkon" P-100, "Arkon" M-90, and "Arkon" M-100, available from Arakawa Chemical Co.; hydrogenated polyterpene resins such as "Nirez" K-85, "Nirez" K-105, and "Nirez" K-110, available from Reichhold Chemicals, Inc.; and hydrogenated aliphatic and aliphatic/aromatic resins such as ECR-142H and ECR-143H, available from Exxon Chemical Co. Preferred tackifying resins include the aliphatic hydrocarbon resins, the hydrogenated resins, and the polyterpene resins. Especially preferred are the aliphatic hydrocarbon resins.

The liquid plasticizer oils suitable for use in the adhesive of the invention include naphthenic oils such as "Shellflex" 371, available from Shell Chemical Co., paraffinic oils, aromatic oils, and mineral oils such as "Kaydol" oil, available from Witco Chemical Corp. Preferred liquid plasticizers include naphthenic oil and mineral oil.

THE DRAWING

The invention may be more easily understood in reference to the following drawing, in which:

FIG. 1 is a schematic view of a disposable diaper as it would appear while being worn by a person.

The disposable diaper shown in FIG. 1 is a conventional three layer composite including a liquid-permeable user-contacting topsheet 12, a liquid-impervious outer shell (backsheet) 14, and an absorbent layer there-between (not shown). At the back 18 of the diaper are corners 20 that overlap the front of the diaper 22 at corners 28 when the diaper is worn as shown. On the topsheet side of each corner 20 is placed a patch of the inventive adhesive 24. On the outer shell 14 at the front 22 of the diaper are two patches 26 of the inventive adhesive. The patches are placed on the diaper such that they will come into contact when the diaper is worn as shown.

The overlapping portions of the adhesive patches should provide a force to peel generally from 2 to 12N, preferably from 5 to 7N. To provide this peel force resistance and still provide for adjustability, the adhesive patches are placed as is shown in FIG. 1. Each patch would be preferably from 3 to 6 cm in length and from 1.5 to 3 cm in width. The lengthwise directions of the patches are preferably orthogonal to each other. This orientation will provide the greatest degree of adjustability for the preferred patches. Where the patches are so oriented and overlap over an entire width portion, the area of contact will be from 1.75 $cm^2$ to 9 $cm^2$ for rectilinear shaped patches. Generally this degree of overlap provides sufficient peel resistance for use as a diaper closure system while avoiding excessive or wasteful use of the adhesive.

Testing

Some tapes bearing the adhesive of the invention were subjected to one or more of the following tests:

Probe Tack Value

This is run according to ASTM D-2979 except using a Polyken Probe Tack tester with a polypropylene probe at a 1 cm/second probe speed, a 1 second dwell time, and a 100 gram/$cm^2$ load.

90° Peel Value

This is run according to PSTC-5 using a polyethylene substrate to which the test tape was applied using a 2-kg hard rubber roller, one pass in each direction at 30 cm/min. An adhesive which has a 90° Peel Value of from 2 to 8N/25 mm should be useful for making note pads of repositionable sheets like POST-IT TM note pads, because such adhesive-bearing sheets should adhere well to paper and other substrates while being removable without picking fibers, even after prolonged periods of time. When the 90° Peel Value is from 0 to 2N/25 mm, the adhesive would be most useful in the above-described adhesive-to-adhesive diaper closure as these are the least likely to adhere to ordinary packaging materials or to the non-adhesive surfaces of the diaper and hence will not require the use of a protective tape. However, protective tapes can be avoided with even higher peel values. For example, repositionable adhesive formulations may adhere to the diaper parts, however, this may be used to advantage in keeping the diaper folded or at worst be ignored as not affecting tape performance.

180° Peel Value

This is run according to ASTM D-1000 except that the adhesive tape is applied to various substrates using a 2-kg hard rubber roller, one pass in each direction at 30 cm/min, and testing was carried out after less than 20 minutes dwell at ordinary room temperature. The peel rate is 30 cm/min when the substrate is paper and 225 cm/min when the substrate is metal or plastic.

Tapes are also tested after two weeks of accelerated aging at 120° F. (49° C.) and then allowed to cool to room temperature for testing.

180° Dynamic Shear Value

This value was determined using ASTM Test Method D3528-76 at a crosshead speed of 10 inches (25 cm) per minute.

T-Peel Value

This value was determined using ASTM Test Method D1876-72 at a crosshead speed of 10 inches (25 cm) per minute.

Self-Adhesion Peel Value with the adhesive layers of two pieces of the same adhesive tape face-to-face, a 2-kg hard rubber roller is applied, one pass in each direction at 30 cm/min. The resulting sandwich is tested for T-peel by ASTM D-1876 at 30 cm/min.

Shear Adhesion Value

A one-inch square (2.54 cm-square) area of a test tape is laid with its adhesive layer against an embossed polyethylene substrate that is used as the backsheet of LUV's brand disposable diapers manufactured by Procter and Gamble and is about 30 $\mu$m thick. To enhance the stiffness of the substrate, the polyethylene substrate is laminated to a pressure-sensitive adhesive tape, viz., Release Tape Y-9378 manufactured by 3M Co. On the side opposite the reinforcing tape, the test tape is rolled down onto the polyethylene substrate with a 2-kg hard rubber roller, one pass in each direction at 30 cm/min. The laminated substrate and the test tape are hung vertically in a 40° C. oven for 15 minutes and a 500-gram weight is promptly hung from the test tape. The time for the weight to drop at 40° C. is the Shear Adhesion Value.

The following examples, in which all parts are by weight, are given by way of illustration and are not intended to limit the scope of the invention in any way. Commercial materials used in the examples were:

| ELASTOMERIC BLOCK COPOLYMERS | | MTg |
|---|---|---|
| "Finaprene" 424 | Styrene/isoprene block copolymer | 215K |
| "Kraton" 1101 | Styrene/butadiene block copolymer | 188K |
| "Kraton" 1107 | Styrene/isoprene block copolymer | 215K |
| "Kraton" 1111 | Styrene/isoprene block copolymer | 215K |
| "Kraton" 1657 | Styrene/ethylene-butylene block copolymer | 215K |
| "Quintac" 3430 | Styrene/isoprene block copolymer | 215K |
| SOLID TACKIFIER RESINS | | Tg |
| "Arkon" P-90 | Hydrogenated hydrocarbon | 309K |
| "Escorez" 1310 | C5 aliphatic | 314K |
| "Escorez" 5300 | Hydrogenated hydrocarbon | 323K |
| "Foral" 85 | Rosin ester | 313K |
| "Piccolyte" HM-105 | Styrenated terpene | 327K |
| "Regalite" 355 | Hydrogenated rosin acid | 318K |
| "Regalrez" 1094 | Hydrogenated hydrocarbon | 310K |
| "Wingtack" 95 | C5 aliphatic | 323K |
| "Wingtack Plus" | C5 aliphatic | 315K |
| "Zonarez" A-100 | Alpha-pinene | 328K |
| LIQUID TACKIFIER RESINS | | |
| ECR-143H | Hydrogenated hydrocarbon | 247K |
| "Escorez" 2520 | Aromatic/aliphatic | 253K |
| "Hercoflex" 500 | Rosin ester | 238K |
| "Wingtack" 10 | C5 aliphatic | 245K |
| "Zonarez" A-25 | Alpha-pinene | 251K |
| LIQUID PLASTICIZER OILS | | |
| "Kaydol" Oil | Mineral oil | 199K |
| "Shellflex" 371 | Naphthenic oil | 209K |
| ANTIOXIDANTS | | |
| "Irganox" 1076 | Hindered Phenol (available from Ciba-Geigy) | |
| "Irganox" 1010 | Hindered Phenol | |

EXAMPLES 1-18

Eighteen adhesive compositions were prepared by dissolving in toluene the components of the formulations given in Table I. One part of "Irganox" 1076 was added to each adhesive composition. Each adhesive solution was 65% by weight of solvent. Tape samples were prepared by coating the adhesive solutions onto a matte-finish cast-polypropylene backing having a thickness of 100 μm. The coating weight of the adhesive after drying at 60° C. for 5 minutes was about 3.5 mg/cm$^2$.

Results of testing the tapes of Examples 1-18 are reported in Table II.

EXAMPLES 19-22

A series of adhesive compositions was made as reported in Table III, and each was dissolved in toluene to a total solids concentration of 25%, with 0.5% of "Irganox" 1010 added to stabilize the adhesive against aging. Each composition was then coated onto a 25 μm thick biaxially oriented poly(ethylene terephthalate) backing and dried to a dry coating weight of about 1.0 mg/cm$^2$. The blocks in the star block copolymer used in Examples 20-22 have a linear configuration, with the isoprene chain capped on each end with styrene chains and were prepared in accordance with the procedure outlined in U.S. Pat. No. 4,780,367, the substance of which is incorporated herein by reference, using a divinylbenzene catalyst to yield a polymer with 16.8% styrene and the remainder predominately isoprene. Results of testing each of Examples 19-22 for 180° Peel Value are reported in Table IV.

TABLE I

| (Compositions for Examples 1-9 in Parts) | | | | | | | | | |
|---|---|---|---|---|---|---|---|---|---|
| Example | 1 | 2 | 3 | 4 | 5 | 6 | 7 | 8 | 9 |
| "Finaprene" 424 | 60 | | | | | | | | |
| "Kraton" 1107 | | 75 | 50 | 65 | 40 | 80 | | | |
| "Kraton" 1111 | | | | | | | 50 | 45 | 80 |
| "Escorez" 2520 | | 23 | 47 | 19 | | | | | |
| "Kaydol" Oil | | | | | | | 31 | 26 | |
| "Shellflex" 371 | | | | | 43 | 7 | | | |
| "Zonarez" A-25 | 32 | | | | | | | | 16 |
| "Arkon" P-90 | | 2 | 3 | 16 | | | | | |
| "Escorez" 1310 | 8 | | | | | | | | |
| "Escorez" 5300 | | | | | | | 19 | 29 | |
| "Wingtack Plus" | | | | | 17 | 13 | | | |
| "Zonarez" A-100 | | | | | | | | | 4 |
| Composite Midblock Tg (Kelvin) | 235 | 225 | 235 | 235 | 225 | 225 | 225 | 235 | 225 |

| (Compositions for Examples 10-18 in Parts) | | | | | | | | | |
|---|---|---|---|---|---|---|---|---|---|
| Example | 10 | 11 | 12 | 13 | 14 | 15 | 16 | 17 | 18 |
| "Kraton" 1101 | | | | | | 20 | 50 | | |
| "Kraton" 1111 | 50 | 70 | | | | | | | |
| "Kraton" 1657 | | | | | | | | 70 | 40 |
| "Quintac" 3430 | | | 75 | 40 | 60 | | | | |
| ECR-143H | | | | | | | | 29 | 58 |
| "Shellflex" 371 | | | | | | 57 | 23 | | |
| "Wingtack" 10 | | | 20 | 56 | 24 | | | | |
| "Zonarez" A-25 | 48 | 16 | | | | | | | |
| "Arkon" P-90 | | | | | | | | 1 | 2 |
| "Piccolyte" HM-105 | | | | | | 23 | 27 | | |
| "Regalrez" 1094 | | | 5 | 4 | 16 | | | | |
| "Zonarez" A-100 | 2 | 14 | | | | | | | |
| Composite Midblock Tg (Kevlin) | 235 | 235 | 225 | 235 | 235 | 225 | 225 | 225 | 235 |

TABLE II

| Example | Probe Tack (N) | 90 Peel Value (N/25 mm) | Shear Adhesion Value (minutes) | Self-Adhesion Peel Value (N/25 mm) |
|---|---|---|---|---|
| 1 | 4.2 | 1.4 | 2 | 2.2 |
| 2 | 0.9 | 0.3 | <1 | 2.1 |
| 3 | 4.5 | 1.1 | 2 | 2.2 |
| 4 | 3.3 | 1.4 | 1 | 1.6 |
| 5 | 3.2 | 0.4 | 3 | 1.6 |
| 6 | 1.6 | 1.0 | 1 | 1.0 |
| 7 | 2.2 | 0.7 | 3 | 0.5 |
| 8 | 6.5 | 2.0 | 26 | 0.9 |
| 9 | 0.9 | 0.3 | 16 | 1.2 |
| 10 | 3.5 | 2.0 | 2 | 0.9 |
| 11 | 3.0 | 1.5 | 25 | 1.6 |
| 12 | 1.1 | 0.4 | 1 | 0.8 |
| 13 | 5.9 | 2.7 | 6 | 2.5 |
| 14 | 3.9 | 1.9 | 11 | 2.7 |
| 15 | 2.9 | 0.2 | <1 | 0.2 |
| 16 | 2.6 | 0.8 | <1 | 0.6 |
| 17 | 0.2 | 0.1 | <1 | 2.3 |
| 18 | 2.9 | 0.4 | 11 | 3.4 |

TABLE III

| (Compositions for Examples 19-22) | | | | |
|---|---|---|---|---|
| Material | 19 | 20 | 21 | 22 |
| "Kraton" 1107 | 80 | | | 17 |
| Star block polymer of styrene/isoprene | | 35 | 20 | 25.5 |
| "Wingtack Plus" | 17.4 | 0.3 | 1.7 | 0.3 |
| "Wingtack" 10 | 2.6 | 64.7 | 78.3 | 57.2 |
| CMTg | 230 | 235 | 240 | 232.5 |

TABLE IV

| | (180° Peel Value in O2/g) | | | |
|---|---|---|---|---|
| Substrate | 19 | 20 | 21 | 22 |
| Paper | 1.7 | 3.2 | 5.0 | 2.4 |
| After aging | 4.1 | 8.9 | 6.6 | 7.0 |
| Stainless Steel | 16 | 11 | 25 | 17 |

TABLE IV-continued

| | (180° Peel Value in 0Z/g) | | | |
|---|---|---|---|---|
| Substrate | 19 | 20 | 21 | 22 |
| After aging | 31 | 25 | 35 | 28 |
| BOPP | 19 | 13 | 24 | 20 |
| After aging | 18 | 19 | 26 | 20 |
| PET | 28 | 18 | 23 | 22 |
| After aging | 28 | 29 | 35 | 27 |

Paper = ordinary bond copypaper
BOPP = biaxially oriented polypropylene
PET = biaxially oriented poly(ethylene terephthalate)

The data reported in Table IV show that each of the adhesives of Examples 19–22 has low adhesion to paper and other substrates and has low adhesion build-up with time evidenced by low adhesion after accelerated aging for two weeks at 49° C. This demonstrates that the adhesive of any of Examples 19–22 should be a suitable substitute, in repositionable note pads, for the adhesive of the above-cited Silver patent, even though these are not preferred examples of such substitute adhesives.

EXAMPLE 23

A handspread of 50% solution in toluene of 70 parts of "Kraton" 1657 and 30 parts of "Res" D-2084 was pulled onto biaxially oriented poly(ethylene terephthalate) film having a thickness of 2.5 μm. The dried coating weight was about 24 g/m². This adhesive had:
CMTg=238 Kelvin
180° Dynamic Shear Value to itself=588N/cm²
T-Peel Value=6.5N/25 mm

Comparative Examples A–G

A series of tapes were made in the same way as the tapes of Examples 1–18 except using adhesive compositions indicated in Table V. Some of the adhesive compositions were as taught in the prior art as follows:

| Comparative Example | Adhesive as Taught in |
|---|---|
| F | Sample 10 of Example III in U.S. Pat. No. 3,954,692 (Downey) |
| G | Example 4 of U.S. Pat. No. 3,932,328 (Korpman) |

TABLE V

| | (Compositions in Parts) | | | | | | |
|---|---|---|---|---|---|---|---|
| Comparative Example | A | B | C | D | E | F | G |
| "Finaprene" 424 | 40 | | | | | | |
| "Kraton" 1107 | | 50 | | | | 100 | 100 |
| "Quintac" 3430 | | | 40 | 30 | 40 | | |
| "Wingtack" 10 | | | | 26 | 11 | | 40 |
| "Zonarez" A-25 | 22 | | | | | | |
| "Kaydol" Oil | | | 6 | | 20 | | |
| "Shellflex" 371 | | 8 | | | | | |
| "Wingtack" 95 | | | | | | 100 | 100 |
| "Escorez" 1310 | 38 | | | | | | |
| "Regalite" 355 | | | 54 | | | | |
| "Regalrez" 1094 | | | | 44 | 49 | | |
| "Wingtack Plus" | | 42 | | | | | |
| Composite Midblock Tg (Kelvin) | 258 | 250 | 262 | 260 | 260 | 254 | 254 |

Testing of comparative example A–G is reported in Table VI.

TABLE VI

| Example | Probe Tack (N) | 90° Peel Value (g/25 mm) | Shear Adhesion Value (minutes) | Self-Adhesion Peel Value (N/25 mm) |
|---|---|---|---|---|
| A | 13 | 7.3 | >1000 | 15 |
| B | 10 | 4.6 | >1000 | 12 |
| C | 10 | 13.6 | >1000 | 12 |
| D | 9 | 9.3 | >1000 | 18 |
| E | 12 | 8.0 | >1000 | 17 |
| F | 11 | 4.9 | >1000 | 18 |
| G | 10 | 7.8 | >1000 | 16 |

As indicated in Tables II and VI, comparative Examples A through G exhibit tack, peel, shear and self-adhesion values that are substantially greater than Example 1 through 18 and are typical of conventional pressure-sensitive adhesives that are based on elastomeric block copolymers.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A low-tack or no-tack adhesive consisting essentially of a composition of by weight:
   from 20 to 80 parts of at least one elastomeric block copolymer selected from the group consisting of styrene/butadiene and styrene/isoprene block copolymers, and
   correspondingly from 80 to 20 parts of tackifying material selected from the group consisting of tackifier resin and a blend of tackifier resin and liquid plasticizer oil, wherein the tackifier comprises 0 to 35 parts of a solid tackifier resin and from 0 to 80 parts of a liquid tackifying resin or plasticizing oil, and wherein the tackifier resin is selected from the group consisting of aliphatic hydrocarbon resins from the polymerization of unsaturated species with four to six carbon atoms, rosin esters and acids, aliphatic/aromatic liquid tackifiers, polyterpene tackifiers, hydrogenated tackifying resins, hydrogenated polyterpene resins and hydrogenated aliphatic and aliphatic/aromatic resins, and the liquid plasticizer oils are selected from the group consisting of mineral oil, naphthenic oil, paraffinic oil, and aromatic oils, and mixtures thereof, which adhesive has a composite midblock glass transition temperature (CMTg) from 225 Kelvin to 240 Kelvin when the adhesive is based on styrene/isoprene block copolymers and a CMTg from 215 Kelvin to 235 Kelvin when the adhesive is based on styrene/butadiene block copolymers to provide an adhesive having no tack or low tack, which adhesive has a 90 degree peel value (as herein defined) of 0.1 to 2.7N/25 mm and a self-adhesion value (as herein defined) of from 0.2 to 3.4N/25 mm.

2. An adhesive as defined in claim 1 and having a 90 degree Peel Value (as herein defined) of 0.1 to 2N/25 mm.

3. An adhesive as defined in claim 1 wherein the elastomeric block copolymer has a configuration selected from the group consisting of linear diblock and triblock, radial, star, and tapered block geometries.

4. An adhesive as defined in claim 1 and containing both a tackifier resin and a liquid plasticizer oil.

5. An adhesive as defined in claim 1 and comprising form 55 to 80 parts by weight of the elastomeric block copolymer.

6. An adhesive as defined in claim 5 wherein the CMTg is within 10° Kelvin of the top of an aforementioned range.

7. An adhesive as defined in claim 1 and comprising from 20 to 45 parts by weight of the elastomeric block copolymer.

8. An adhesive as defined in claim 7 wherein the CMTg is within 10 Kelvin of the bottom of an aforementioned range, and the adhesive is a pressure-sensitive adhesive.

* * * * *

UNITED STATES PATENT AND TRADEMARK OFFICE
CERTIFICATE OF CORRECTION

PATENT NO. : 5,389,438

DATED : February 14, 1995

INVENTOR(S) : John A. Miller and George J. Clements

It is certified that error appears in the above-indentified patent and that said Letters Patent is hereby corrected as shown below:

Col. 10, line 65, (Table IV) "02/g" should read --Oz/g--.

Col. 11, line 3, (Table IV Continued) "02/g" should read --Oz/g--.

Col. 11, line 28, "2.5" should read --12.5--.

Col. 12, line 51, "which" should begin on a new line.

Col. 13, line 4, "form" should read --from--.

Signed and Sealed this

Ninth Day of April, 1996

Attest:

BRUCE LEHMAN

*Attesting Officer*  *Commissioner of Patents and Trademarks*